United States Patent [19]
Vince

[11] Patent Number: 5,163,953
[45] Date of Patent: Nov. 17, 1992

[54] TOROIDAL ARTIFICIAL HEART VALVE STENT

[76] Inventor: Dennis J. Vince, 10-943 West Broadway, Vancouver, B.C., Canada, V5Z 1K3

[21] Appl. No.: 833,543
[22] Filed: Feb. 10, 1992
[51] Int. Cl.⁵ .............................................. A61F 2/24
[52] U.S. Cl. ...................................... 623/2; 623/900
[58] Field of Search ................................. 623/2, 900

[56] References Cited

U.S. PATENT DOCUMENTS 4,038,703  8/1977  Bokros ..................................... 623/2
4,106,129  8/1978  Carpentier et al. ..................... 623/2

Primary Examiner—Randy C. Shay
Attorney, Agent, or Firm—Townsend and Townsend

[57] ABSTRACT

A stent for a heart valve. The valve has a flap valve of biological material. The stent has a generally toroidal body formed of a flexible coil of wire. A plurality of posts extend upwardly from the body to mount the flap valves. The stent in combination with a percutaneous balloon dilatable catheter is also described. The catheter is positioned intraluminal of the valve and dilation of the balloon exerts stress to overcome the elastic limit of the stent to increase stent circumference.

5 Claims, 2 Drawing Sheets

TOROIDAL ARTIFICIAL HEART VALVE STENT

FIELD OF THE INVENTION

This invention relates to a stent for an artificial heart valve.

DESCRIPTION OF THE PRIOR ART

Although heart replacement operations receive considerable publicity by far the more common operation in heart surgery is replacement of one or more of the valves controlling blood flow in the heart. The valves are the tricuspid, the mitral, the pulmonic and the aortic valves.

The heart may be considered as a simple pump consisting of fours chambers, the left and right atria and the left and right ventricles with the valves located between the chambers and controlling blood flow.

The valves used to replace natural heart valves are of two general types, bioprosthetic valves and mechanical valves. The former are valves that resemble normal heart valves and use valve leaflets (or flaps) of tissue or similar biological material. Mechanical valves usually employ disc valves manufactured of synthetic biocompatible material. Ball and cage valves have been used but use of these is decreasing.

Early heart valve replacement used aortic valves unsupported by a frame or stent. However, the replacement operation was difficult to perform. It was found that the operation was easier to perform and the valve functioned better if the valve was supported by a stent. The valve is sutured to the stent. Animal materials are now used, such as bovine or porcine pericardium. Early sterilization problems of the valves have been overcome but calcification and deterioration of artificial valve leflets remains a significant problem. Fatigue fracture of the stents and difficulty in insertion of circular stents in non-circular sites also remains a problem.

During cardiac systolic contraction, extremely high forces are applied at the point where the valve is attached to the stent. In the prior art the preffered stent material is titanium and the stent is rigid.

Thus the current, most common, prior art comprises a circular component or stent that forms the base of the valve with three posts, called commissural posts, extending from the stent and receiving the leaflet tissue that forms the flap valve of the artificial heart valve.

Because of its rigidity, the stent has no dynamic function in the action of valve leaflets; it is merely a frame. Similarly the commissural post are rigid and fixed in their position of attachment to the circular base.

BRIEF SUMMARY OF THE INVENTION

The present invention seek to improve on the prior art by providing a stent that assists in the operation of the artificial valve rather than merely acting as a frame.

Accordingly, and in a first aspect, the present invention is a stent for a heart valve, the valve having flap valves of biological material, the stent comprising, a generally toroidal body formed of a flexible coil of wire and a plurality of posts extending upwardly from the toroidal body to mount the flap valves.

Preferably, the stent is of unitary construction with the plurality of posts formed by the wire of the generally toroidal body.

Preferably there are three posts dividing the generally toroidal body into three segments.

The generally toroidal body of the stent is desirably ensheathed in a Silastic tube. (Silastic is a trademark of Dow Corning for a silicone polymer). Such a material is biologically compatible. It prevents tissue ingrowth into the stent. Preferably the Silastic sheath is covered with a suitable biocompatible material selected to promote tissue endothelialization. The latter forms a sewing ring to enable surgical installation of the valve as with conventional bioprosthetic valves. The sewing ring technique is well known in the art.

In a further aspect, the invention is a stent as defined above in combination with a percutaneous balloon dilatable catheter, intraluminal of the valve, dilation of the balloon exerting stress to overcome the elastic limit of the stent, resulting in permanent extension of the helix and thus permanently increasing stent circumference.

BRIEF DESCRIPTION OF THE DRAWINGS

The invention is illustrated, by way of example, in the accompanying drawings in wich.

DESCRIPTION OF THE PREFERRED EMBODIMENTS

Figure 1:
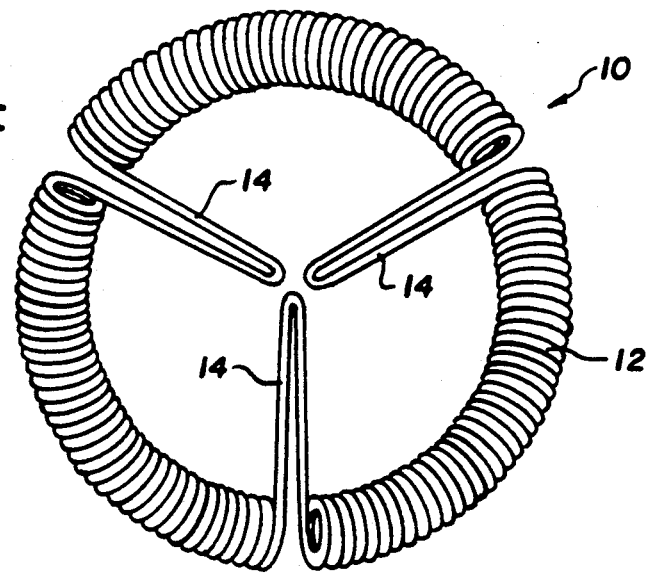
FIG. 1 is a plan view of a stent according to the present invention.
Figure 2:
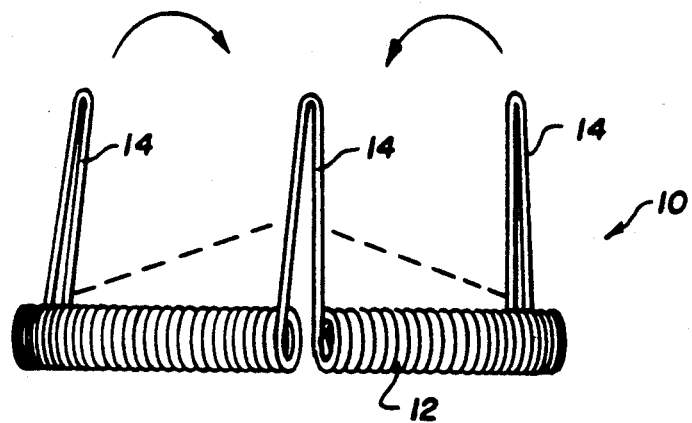
FIG. 2 is a side elevation of the stent of FIG. 1.
Figure 3:
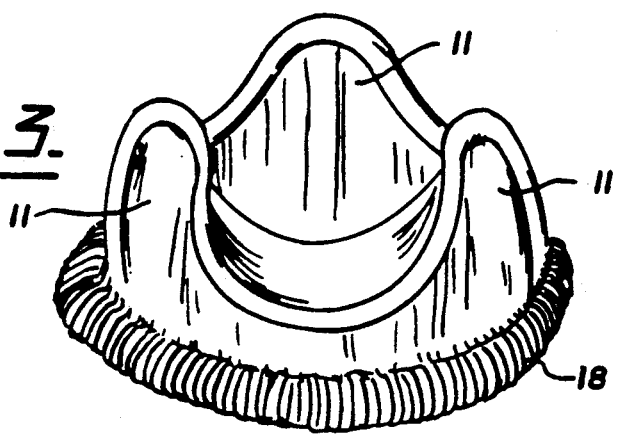
FIG. 3 shows the stent of FIG. 1 in position in a heart valve.

FIGS. 1 and 2 show a stent 10 for a heart valve. FIG. 3 shows the stent 10 in place in a valve. The valve has flaps 11 of a biological material acting as valves in replacement of the natural valves. The stent 10 comprises a generally toroidal body 12 formed of a flexible coil of wire. In the illustrated embodiment a plurality of cqmmissural posts 14 extend upwardly from the body 12 to mount the flaps 11. The stent 10 has a unitary structure. The body 12 is made of a coil of wire and the same wire is extended upwardly from the body 12 to form the commissural posts 14. The illustrated embodiment shows three posts 14 dividing the body 12 into three segments.

Figure 4:
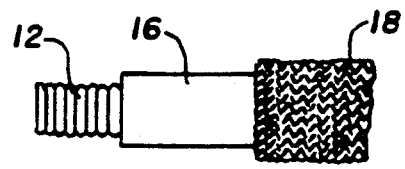
FIG. 4 shows a detail of the stent.
Figure 5:
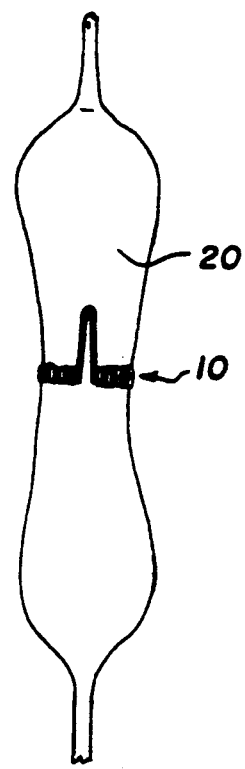
FIG. 5 illustrates the use of a balloon catheter with the stent of the present invention.
Figure 6:
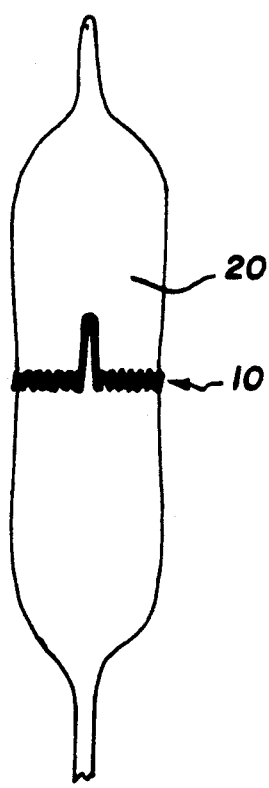
FIG. 6 illustrates further the use of a balloon catheter with the stent of FIG. 1.

The body 12 of the stent 10 is covered in a Silastic material 16, as shown in FIG. 4. There is also a sewing ring 18, as shown in FIGS. 3 and 4, to allow stitching of the stent 10 in place in the heart.

A heart valve supported by a stent 10 according to the present invention functions as follows.

During ventricular systole, as the intraluminal pressure increases, circumferentisl stress (hoop stress) develops on the circumference of the stent 10. This stress is transmitted as axial stress to the body 12. The body 12 expands and the energy is stored all along the body 12 as torsional stress. The circumference thus increases. This in turn increases the valve orifice and reduces flow resistance from the ventricle through the valve during ventricular ejection.

During ventricular diastole, as the intraluminal pressure falls, the fall in hoop stress allows the stored energy in the body 12 to decrease the circumference of the stent 10 in an elastic recovery. The orifice in the valve reduces and resistance to backward flow of the valve (regurgitation) is thus increased.

Thus, the present invention provides a variable orifice valve. The orificie varies in a direction to encourage forward flow, reduced regurgitation and complement the flap valve action. In addition, as the orifice is reduced, the commissural posts 14 are moved towards the centre of the orifice, as shown by the arrows in FIG. 2. Thus the valve cusp's free edges will move closer together and the coaptational surfaces are increased. This improves diastolic function by limiting regurgitation.

During ventricular systole, with ventricular ejection through the valve orifice, the ejected stream will displace the valve cusps outwardly. The valve cusps, which are attached to the commissural posts 14, are rotated outwardly by the forces. The posts 14 are an integral part of the stent 10 and thus have flexibility. This outward rotation of the commissural posts 14 will take place as a result of torsional forces all around the circumference of the body 12. All three posts 14 and their attached valves 11 are rotated outwardly uniformly. This increases the orifice size, reducing resistance to flow.

In contrast, in the prior art valve, with a non-flexible stent, the commissural posts are held in their resting position at systole and diastole. This results in a reduction of the valve orifice.

During ventricular diastole the reverse dynamics occur. The torsional energy stored in the body 12 rotates the commissural posts 14 toward the centre of the orifice. The pressure distal to the valve forces the cusps and the attached commissural posts 14 inwardly and the valve closes. The distribution of these forces by the body 12 to all three commissural posts 14 ensures uniform positioning of the commissural posts 14 and their attached valve leaflets 11. The commissural posts 14 abut and prevent prolapse during valve closure.

A very useful aspect of the invention is illustrated in FIGS. 3 and 4. The elasticity of the stent 10 permits enlarging of the circumference of the valve and permanently increasing the orifice. A percutaneous balloon dilation catheter 20 can be inserted intraluminal to the valve. Dilation of the balloon 20 exerts sufficient stress to overcome the elastic limit of the body 12 of the stent 10 and permanently expands the circumference of the stent by exceeding the plastic onset of the helix. The balloon catheter 20 is then deflated and removed, leaving a permanently increased valve orifice. The additional coaptational surface of the valve, which results from the special properties of the flexible stent, provides adequate appositional surfaces to ensure diastolic competence of the enlarged valve.

Thus, the present invention provides an artificial heart valve stent having new and valuable properties, including:

The flexible circular body 12 allows insertion into a non-circular anatomic site.

The body 12 expands and contracts with variations in the intracavitational pressure increasing the effective valve orifice in systole and decreasing the effective valve orifice in diastole Dynamic movement of the commissural posts 14 is induced by blood flow acting on the valve leaflets 11 attached to the commissural posts 14. During systole the commissural posts rotate outwardly and increase the effective valve orifice size. During diastole the commissural posts 14 are rotated inwardly and reduce the effective valve orifice size. At the same time the valve leaflets are opposed and the appositional surfaces are increased. This dynamic movement is enabled by the commissural posts 14 being an integral part of the stent 10.

The body 12 of the stent 10 can be permanently dilated with an intraluminal balloon dilator by exceeding the elastic limits of the helix and introducing plastic onset in the body 12.

The commissural posts 14, being an integral part of the stent 10, permit flexing stresses to be distributed along the body 12. This reduces the risk of stress fracture of the commissural posts 14 at their attachment to the body 12.

I claim:

1. A stent for a heart valve, the valve having flap valves of biological material, the stent comprising:
    a generally toroidal body formed of a flexible coil of wire; and
    a plurality of posts extending substantially parallel to the axis of the toroidal body to mount the flap valves.

2. A stent as claimed in claim 1 having a unitary structure with the plurality of posts formed by the wire of the generally toroidal body.

3. A stent as claimed in claim 2 in which there are three posts dividing the toroidal body into three segments.

4. A stent as claimed in claim 1 covered in a flexible silicone sheath.

5. A stent as claimed in clim 1 in combination with a percutaneous balloon dilatable catheter, intraluminal of the valve, dilation of the balloon exerting stress to overcome the elastic limit of the stent to increase stent circumference.

* * * * *